United States Patent
Robertson

[11] 3,960,835
[45] June 1, 1976

[54] ZEARALINE GLYCOSIDE COMPOUNDS

[75] Inventor: Donald E. Robertson, Terre Haute, Ind.

[73] Assignee: Commercial Solvents Corporation, Terre Haute, Ind.

[22] Filed: Jan. 18, 1974

[21] Appl. No.: 434,405

[52] U.S. Cl. .............................. 260/210 R; 424/180
[51] Int. Cl.² ......................................... C07H 15/00
[58] Field of Search ................................ 260/210 R

[56] References Cited
UNITED STATES PATENTS

| | | | |
|---|---|---|---|
| 3,152,115 | 10/1964 | Morel et al. | 260/210 R |
| 3,356,674 | 12/1967 | Ikeda et al. | 260/210 R |
| 3,758,455 | 9/1973 | Arita | 260/210 R |

*Primary Examiner*—Johnnie R. Brown
*Attorney, Agent, or Firm*—Morton, Bernard, Brown, Roberts and Sutherland

[57] ABSTRACT

Compounds of the formula:

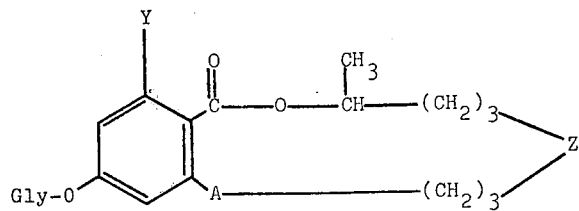

wherein —A— is either —$CH_2$—$CH_2$— or —CH=CH—, >Z is either >$CH_2$, >C=O or >CH—OH, Y is —H or —OR' wherein R' can be hydrogen, alkyl, alkanoyl, aryl, or aryl alkyl, and Gly is a glycosyl group, which exhibit anabolic and estrogenic activity, are provided, as well as processes for their preparation and compositions containing them which are useful as ruminant growth promoters.

16 Claims, No Drawings

ZEARALINE GLYCOSIDE COMPOUNDS

This invention relates to novel organic compounds having anabolic and estrogenic properties, to a process for their preparation, and to compositions containing them. More particularly, it relates to novel glycosides. The compounds included within the scope of the present invention, hereinafter referred to as the "G" compounds, are those of the formula:

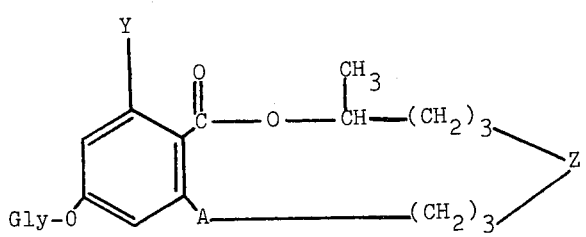

wherein —A— is either —$CH_2$—$CH_2$— or —CH=CH—; >Z is either >$CH_2$>C=O or >CH—OH; Y is —H or —OR', wherein R' is selected from the group consisting of hydrogen; substituted and unsubstituted alkyl, e.g., containing from 1 to about 15 carbon atoms including lower alkyl such as methyl, ethyl, hexyl, etc., and cycloalkyl, particularly monocyclic alkyl of about 5 to 8 carbon atoms, such as cyclopentyl, cyclohexyl, methyl cyclohexyl, etc.; substituted or unsubstituted alkanoyl, generally containing 1 to about 25 or more carbon atoms including lower alkanoyl such as acetyl, propionyl, valeryl, etc.; substituted or unsubstituted aryl, for instance, monocyclic or bicyclic aryl containing about 6 to 15 carbon atoms or more, such as phenyl, tolyl, naphthyl, etc.; and aryl alkyl (that is an alkyl group having an aryl substituent thereon), wherein the aryl substituent may be monocyclic or bicyclic aryl containing about 6 to 15 carbon atoms or more and the alkyl group is generally lower alkyl, for example, 1 to about 6 carbon atoms, such as benzyl, bromobenzyl, benzoyl, tolyl methyl, and the like, and wherein Gly is a glycosyl group of about 4 to 5 ring carbon atoms and is derived from a glycosyl halide-providing glycose. Gly may be represented by the formula

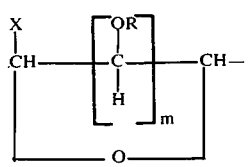

wherein X is —H or —(CHOR)$_n$CH$_2$OR, wherein $n$ is 0, 1 or 2; $m$ is 2 to 3 or more; R can be any of the substituents set forth above for R', and, in addition, can be —NO$_2$.

One method of preparing the G compounds is by reacting a glycosyl halide, which, for instance, may be Gly—Br, with a Zearalin. Zearalin compounds employed in this invention may be represented by the formula:

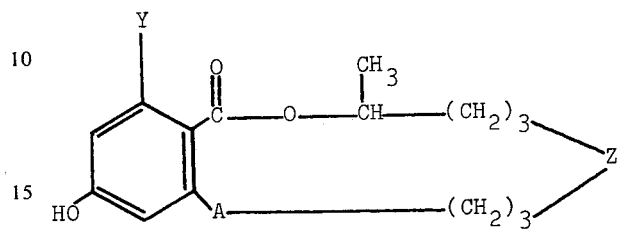

wherein —A—, Y, and >Z are as defined above.

An alternative means of preparation of the G compounds wherein each R is hydrogen, involves reacting a glycosyl bromide, hereabove defined, wherein each R is alkanoyl, for example,

with a Zearalin to yield the G compound wherein each R is alkanoyl, and second, subjecting it to base catalyzed transesterification to convert the alkanoyl groups to hydrogen atoms.

The reaction of the glycosyl halide and the Zearalin to prepare the G compound can generally be effected under condensation (dehydrobromination) conditions, e.g., at about 5° to 90°C., preferably about 10° to 80°C., and preferably with the reactants in solution in solvent-providing amounts of an inert solvent such as a mixture of water and a polar, aprotic solvent, e.g., acetone, dimethylsulfoxide, tetrahydrofuran or dimethylformamide. The solvent is frequently provided in an amount of about 1 to 100 or more, preferably about 3 to 50, times by weight of Zearalin. The reaction mixture also preferably contains an acceptor, such as an alkali metal hydroxide, e.g., sodium hydroxide and potassium hydroxide. The acceptor is employed in an amount of about 0.7 to 2 mole of acceptor per mole of Zearalin. Reaction time will vary, depending upon the particular glycosyl halide, but the reaction will often be complete in about 20 hours or less. The ratios of reactants to be employed in the reaction mixture are generally about 0.8 to 1.5 moles of glycosyl halide per mole of Zearalin.

The transesterification reaction discussed above, by which G compounds wherein each R is hydrogen are prepared, is preferably effected through the use of solvent-providing amounts of a monohydric alkanol of 1 to 5 carbon atoms as both the displacing alcohol and the reaction solvent. The transesterification temperatures generally employed are about room temperature, e.g., 10° to 15°C., to about the refluxing temperature of the solvent. The amount of alkanol employed is preferably sufficient to dissolve substantially all of the ester starting material. Suitable transesterification catalysts include alkali and alkaline earth metal alkoxides and are employed in catalytic amounts, preferably about 0.1 to 2 moles per mole of the ester. Reaction time will vary with temperature, catalyst amounts, etc., but will usually range from about 1 to about 10 hours until completion of reaction.

Recovery and refinement of the G compounds can be by conventional techniques, for example by crystallization, filtration, and recrystallization.

The glycosyl halides and Zearalins employed to make the G compounds can be prepared by known methods. Preferred glycosyl halides are glucopyranosyl bromide and glucopyranosyl bromide derivatives, for instance, 2,3,4,6-tetra-O-acetyl-D-glucopyranosyl bromide.

Zearalins can be prepared, for instance, from zearalenone (—A— is —HC=CH—, >Z is >C=O, and Y is —OH), which can be obtained by cultivation of the microorganism *Gibberella zeae* (Gordon) in a suitable fermentation medium, as described, for example, in U.S. Pat. No. 3,196,019.

Zearalenone may be employed to prepare others of the Zearalins which may be used to provide the G compounds. For instance, the unsaturated carbon bond in the lactone zearalenone ring can be hydrogenated according to the procedure of U.S. Pat. No. 3,239,354. The keto group of zearalenone may be converted to >CHOH by the procedure disclosed in U.S. Pat. No. 3,239,345. The keto group of zearalenone may be converted to $>CH_2$ by the procedure disclosed in U.S. Pat. No. 3,239,341. Replacement of the hydrogen of the hydroxy groups of the Zearalins with an alkyl, alkanoyl, aryl, or aryl alkyl radical is disclosed in U.S. Pat. Nos. 3,239,342, 3,239,347, and the above mentioned patents.

Zearalenone, as obtained by fermentation as in U.S. Pat. No. 3,196,019, is in the trans-configuration. Trans-zearalenone, or Zearalins prepared therefrom, may be converted to the corresponding cis configuration by electromagnetic irradiation of the trans isomer in the 2800–3500 angstrom wave length range, as disclosed in U.S. patent application Ser. No. 317,117, filed Dec. 21, 1972 now abandoned.

Zearalins wherein >Z is >CHOH can, and do, exist in two different diastereoisomeric arrangements based on the substitutions on the >Z carbon atom. Diastereoisomers, or "diamers" as they are commonly called, are stereoisomers which are not enantiomorphs (i.e., are not mirror images). These diamers have different melting points and, for that reason, can be distinguished as the low melting diamer and the high melting diamer. One process for the separation of the diastereoisomers of zearalanol is disclosed in U.S. Pat. No. 3,687,982.

The preferred substituents for Y are those wherein Y is —OR' and R' is hydrogen, lower alkyl, lower alkanoyl or monocyclic aryl lower-alkyl, e.g., benzyl, of 6 to 15 carbon atoms. Preferred glycosyls are those wherein n is 0 and m is 3, for instance, the glucopyranosyls, for instance, D-glucopyranosyl, 2,3,4,6-tetra-O-acetyl-D-glucopyranosyl, and the like.

The G compounds can be administered to ruminants either orally or parenterally in amounts sufficient to enhance the growth rate of the animal. Female ruminants are the preferred hosts for enhanced growth. The amount of G compound administered to an animal varies, of course, upon the animal, the desired rate of growth, and the like. The G compound is frequently administered in an amount of about 1 to 200, preferably 1 to 50 milligrams per head per day.

The G compound can be administered in combination with a pharmaceutically-acceptable carrier. For example, the G compound can be employed as an additive in their feed or as an implant under the skin. For example, the compounds can be blended with ordinary feed which contains nutritional values in an amount sufficient to produce the desired rate of growth, or the compounds can be suspended in a suitable injection suspension medium, such as peanut oil, and injected parenterally. From 2.5 to 50 grams of the compound per ton of feed is typical. When an implant is used, for example a ball or cylindrical implant inserted under the skin on the ear of an animal, the implant will generally contain from 1 mg. to 100 mg. of the compound. Other modes of parenteral administration include intramuscular, intravenous, and intraperitoneal injections.

When a compound of this invention is to be administered to female ruminants in their feed, an animal feed composition may be prepared containing the usual nutritionally-balanced quantities of carbohydrates, proteins, vitamins, and minerals, together with the compound. Some to the usual sources of these dietary elements are grains, such as ground grain and grain by-products; animal protein substances, such as those found in fish meal and meat scraps; vegetable proteins, such as soybean oil meal or peanut oil meal; vitaminaceous materials, e.g., mixture of vitamins A and D, riboflavin supplements and other vitamin B complex members; and bone meal and limestone to provide minerals.

The following examples are offered to illustrate this invention; however, the invention is not limited to the specific materials, amounts, and procedures set forth.

EXAMPLE 1

This example illustrates the preparation of $O^4$-(2,3,4,6-tetra-O-acetyl-D-glucopyranosyl)-zearalenone of the formula:

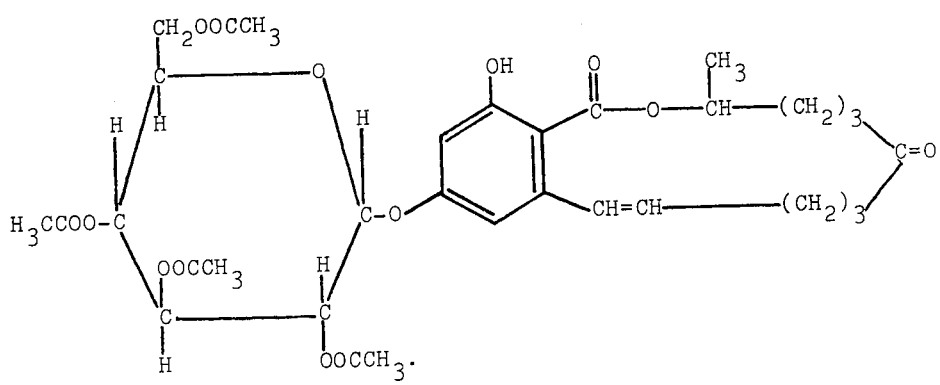

Trans-zearalenone (12.7 g., 0.04 mole) is stirred in water (50 ml.) containing NaOH (1.7 g. of NaOH (95%), 0.04 mole) for several minutes giving a nearly complete solution of the solid. A solution of tetra-O-acetyl-a-D-glucopyranosyl bromide (16.8 g., 0.04 mole, in 80 ml. of acetone) is added producing a clear solution. The solution is stirred at room temperature. After 20–30 minutes, a crystalline precipitate is formed. The mixture is stirred for an additional 2.5 hours and filtered. The cake is washed with 100 ml. of cold water and dried in vacuum, giving 7.78 g. of white crystals, M.P. 176°–182°, which turn slightly yellow at the surface on standing. The crystals are recrystallized from ether to yield 5.47 g. of white, fluffy crystals of $O^4$-(2,3,4,6-tetra-O-acetyl-D-glucopyranosyl)-zearalenone having a melting point of 191°–192°C.

EXAMPLE 2

This example illustrates the preparation of $O^4$-glucopyranosylzearalenone of the formula

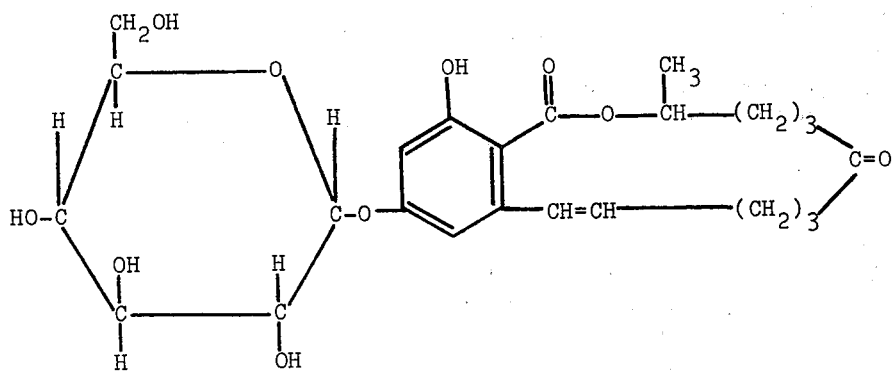

$O^4$-(2,3,4,6-tetra-O-acetyl-D-glucopyronosyl)-zearalenone (8.1 g., 0.012 mole) prepared as in Example 1 is dispersed in 120 ml. of anhydrous methanol under reflux conditions. There is added thereto 6 ml. of 0.2 Normal $NaOCH_3$ in methanol. The dispersion becomes a clear solution within 10 minutes. The solution is refluxed for an additional 25 minutes and then allowed to cool slowly. Crystals form and the mixture is cooled further in ice. The crystals are filtered and dried at 60°C. in vacuum, yielding 4.83 g. of pale yellow $O^4$-glucopyranosylzearalenone in monohydrate form.

EXAMPLE 3

This example illustrates the preparation of $O^4$-(2,3,4,6-tetra-O-acetyl-D-glucopyranosyl)-zearalanol of the formula

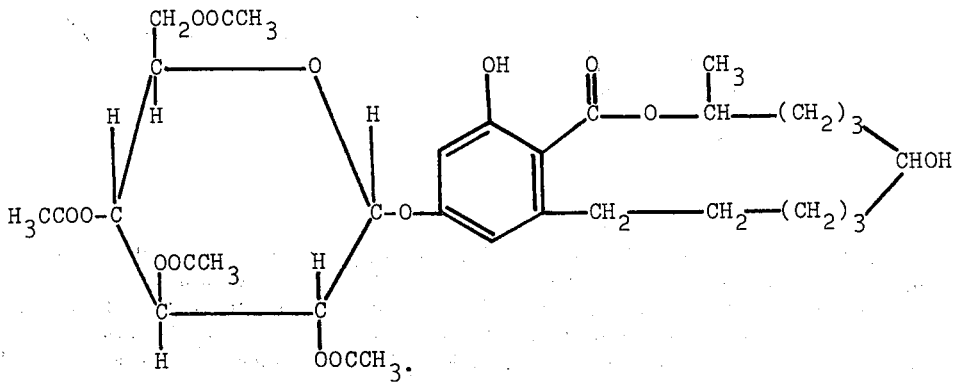

The high melting diamer of zearalanol in the amount of 6.5 g. (0.020 mole) is dissolved in 50 ml. of 0.8 molar aqueous sodium hydroxide solution and 35 ml. of acetone. A solution of 2,3,4,6-tetra-O-acetyl-a-D-glucopyranosyl bromide (8.4 g., 0.020 mole, mp 89°–90°) is added in one portion, and crystals are formed in the orange solution after 1 hour of stirring at room temperature. The mixture is stirred for an additional 1 hour and filtered. The filter cake is washed with water (200 ml.), and dried in vacuo yielding 8.65 g. of a gummy off-white solid. The crude solid is triturated three times with chloroform (50-ml. portions) leaving 3.94 g. of insoluble zearalanol (mp 181°–182°). The extracts are concentrated in vacuo yielding 4.28 g. (87% based on unrecovered starting material) of the crude pale yellow glycoside, mp 161°–163°. Recrystallization to purity from ether yielded $O^4$-(2,3,4,6-tetra-O-acetyl-D-glucopyranosyl)-zearalanol (27% based on unrecovered starting material) as fluffy white crystals having a melting point of 179.5°–180°C.

EXAMPLE 4

This example illustrates the preparation of $O^4$-(2,3,4,6-tetra-O-acetyl-D-glucopyranosyl)-zearalane of the formula

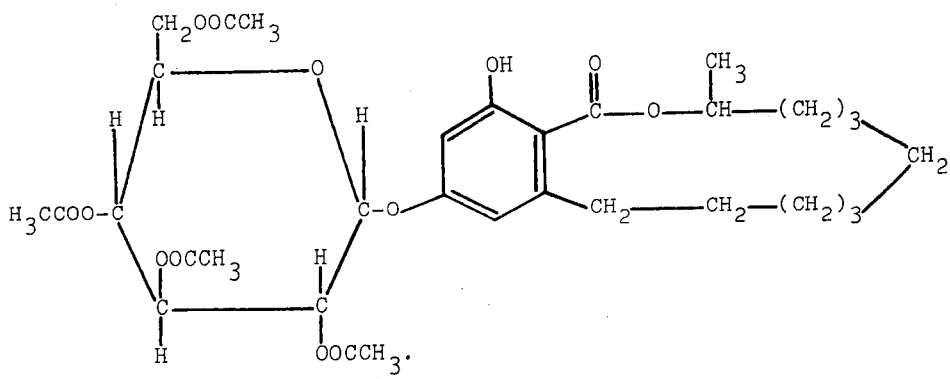

A solution of zearalane (9.2 g., 0.030 mole), triethylamine (3.0 g., 0.030 mole), and (2,3,4,6-tetra-O-acetyl-D-glucopyranosyl)bromide (12.6 g. 0.030 mole) in chloroform (100 ml., anhydrous ethanol free) stirred for 131 hours at ambient temperature and under reflux for 13 hours. Progress of the reaction is followed by thin layer chromatography until the concentration of starting material is not further diminished. The solution is washed twice with 5 percent aqueous sodium hydroxide (100 ml. portions) and with water (100 ml.). The solution is treated with decolorizing carbon (Darco G-60), and dried over calcium sulfate and concentrated in vacuo to yield 15.6 g. of a dark brown glass. The residue still contained some starting material as seen through comparative thin layer chromatographic analysis. Nearly all of this residue is dissolved in 200 ml. of chloroform, and the solution is washed twice with 100 ml. portions of a 5 percent aqueous sodium hydroxide (100-ml. portions) and then with 100 ml. of water. The solution is dried over calcium sulfate and concentrated in vacuo to yield 4.47 g. of brown viscous oil. Crystallization with decolorization with carbon, from ethanol-water yielded 0.70 g. of $O^4$-(2,3,4,6-tetra-O-acetyl-D-glucopyranosyl)-zearalane as white crystals having melting points mp 148°–150°C. and 146°–148°C. in admixture with starting material.

EXAMPLE 5

This example illustrates the preparation of $O^4$-(2,3,4,6-tetra-O-acetyl-D-glucopyranosyl)-zearalanone of the formula

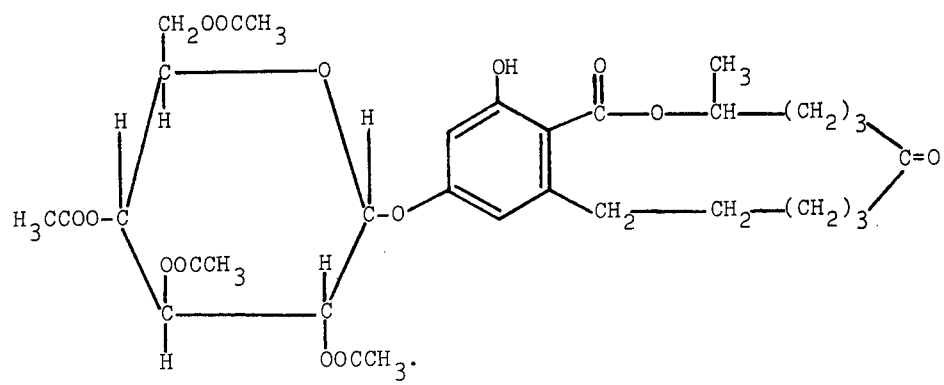

The procedure of Example 1 is repeated, but using 0.02 mole (6.4 g.) of zearalanone instead of zearalenone with the addition of 0.10 g. of potassium iodide to the initial mixture as a catalyst. The initial reaction mixture is stirred for two hours with the formation of crystals within the initial 30 to 35 minutes. Recrystallization from ether of the filtered product yields 2.54 g. of $O^4$-(2,3,4,6-tetra-O-acetyl-D-glucopyranosyl)-zearalanone as white crystals having a melting point of 191°–192°C.

EXAMPLE 6

This example illustrates the estrogenic activities of the compounds prepared in the foregoing examples.

Samples of the compounds are tested for uterotropic activity according to the well known mouse uterine test. This test consists of feeding the test material in admixture with a standard feed to eight, adult, ovariectomized female mice at a ration of 3 grams per day for a 5-day period. On day six, the animals are weighed and sacrificed, and their uteri removed and weighed. Estrogenic activity is confirmed if the uterus of the test mouse is heavier and accounts for a greater percentage of the mouse's body weight than the uterus of a control mouse. Test results are reported in Table I.

TABLE I

| Test Compound | Daily Dose ($\mu$ug./g. feed) | Uterine Wt. (mg.) | % Body Wt. |
|---|---|---|---|
| Control 1 | — | 14.3 | 0.055 |
| Example 1 | 25 | 37.3 | 0.135 |
| " | 50 | 37.8 | 0.148 |
| Control 2 | — | 14.5 | 0.067 |
| Example 2 | 12.5 | 17.1 | 0.089 |
| " | 25 | 27.4 | 0.138 |
| " | 50 | 59.3 | 0.300 |

EXAMPLE 7

Example 6 is repeated except in Runs 4a and 4b in which the compound is administered once a day in a 0.1 ml. of sesame oil by forced feeding or subcutaneous injection. The results are reported in Table II. Zearalenone and various derivatives thereof are provided as a basis for comparison to illustrate the uterotropic activity of the compounds of the present invention. It should be noted for comparative purposes that, for instance, zearalenone has twice as much of the zearalin derivative per unit weight as does $O^4$-(2,3,4,6-tetra-O-acetyl-D-glucopyranosyl)-zearalenone.

milligrams of a pharmaceutically-acceptable carrier for the test compound. Water and basal rations (described below) are then provided ad-libitum. Individual weights and feed conversions are obtained every two weeks. After six weeks, the test is completed and the data analyzed by appropriate statistical methods. The analysis shows a 10.3 percent greater weight gain response in the implanted ewes than in the control.

TABLE II

| Run | Compound | Dose ($\mu$g) | Final Weights A. Body (g) | Final Weights B. Uterine (mg) | Uterine as % of body weight |
|---|---|---|---|---|---|
| 1. | Example 1 | 50 | 27.1 | 30.3 | 0.110 |
|  |  | 500 | — | — | 0.540 |
|  | zearalenone | 25 | — | — | 0.152[a] |
|  | Control | 0 | — | — | 0.057 |
| 2. | Example 1 | 25 | 28.6 | 37.3 | 0.135 |
|  |  | 50 | 25.5 | 37.8 | 0.148 |
|  | zearalenone | 25 | 25.7 | 36.3 | 0.141[a] |
|  | Control | 0 | 26.1 | 14.3 | 0.055 |
| 3. | Example 1 | 6.25 | 19.0 | 13.3 | 0.070 |
|  |  | 12.5 | 18.1 | 13.2 | 0.073 |
|  |  | 25 | 19.6 | 21.9 | 0.112 |
|  | zearalenone | 25 | 19.5 | 41.3 | 0.212[a] |
|  | Control | 0 | 19.4 | 13.9 | 0.072 |
| 4a. | Oral feeding |  |  |  |  |
|  | Example 1 | 25 | 26.4 | 17.2 | 0.065 |
|  |  | 50 | 27.2 | 23.6 | 0.086 |
|  |  | 100 | 26.8 | 28.5 | 0.106 |
|  | zearalenone | 25 | 26.4 | 22.7 | 0.086 |
|  |  | 50 | 27.0 | 21.6 | 0.080 |
|  |  | 100 | 26.6 | 25.6 | 0.097 |
|  | Control | 0 | 26.6 | 17.4 | 0.065 |
| 4b. | Subcutaneous Administration |  |  |  |  |
|  | Example 1 | 12.5 | 26.4 | 19.3 | 0.073 |
|  |  | 25 | 27.2 | 21.8 | 0.080 |
|  |  | 50 | 26.6 | 29.2 | 0.111 |
|  | zearalenone | 12.5 | 27.4 | 21.1 | 0.076 |
|  |  | 50 | 26.6 | 27.8 | 0.101 |
|  |  | 100 | 26.4 | 32.8 | 0.120 |
|  | Control | 0 | 26.8 | 13.8 | 0.052 |
| 5. | Example 2 | 12.5 | 19.2 | 17.1 | 0.089 |
|  | G-1492 | 25 | 19.9 | 27.4 | 0.138 |
|  |  | 50 | 19.8 | 59.3 | 0.300 |
|  | zearalenone | 25 | 20.1 | 46.2 | 0.230[a] |
|  | Control | 0 | 21.5 | 14.5 | 0.067 |
| 6. | Example 3 | 3.1 | 21.0 | 15.9 | 0.076 |
|  |  | 6.25 | 20.7 | 20.0 | 0.096 |
|  |  | 12.5 | 21.7 | 23.6 | 0.112 |
|  | zearalanol (high melting) | 6.25 | 18.5 | 19.5 | 0.105[b] |
|  | zearalenone | 25 | 20.5 | 32.5 | 0.152[a] |
|  | Control | 0 | 20.5 | 12.7 | 0.062 |
| 7. | Example 4 | 25 | — | — | 0.086 |
|  |  | 50 | — | — | 0.102 |
|  |  | 100 | — | — | 0.191 |
|  | zearalenone | 25 | — | — | 0.145[a] |
|  | zearalane | 25 | — | — | 0.141[c] |
|  | Control | 0 | — | — | 0.057 |
| 8. | Example 5 | 12.5 | 22.8 | 26.8 | 0.117 |
|  |  | 25 | 22.9 | 35.8 | 0.156 |
|  |  | 50 | 23.3 | 60.8 | 0.261 |
|  | zearalenone | 25 | 21.9 | 29.1 | 0.135[a] |
|  | zearalenone | 25 | — | — | 0.204[d] |
|  |  | 12.5 | — | — | 0.129[d] |
|  | Control | 0 | 20.4 | 10.3 | 0.051 |

[a]The average normal response for zearalenone, 25$\mu$g is 0.140–0.150%.
[b]The average normal response for zearalanol (HM), 6.25 $\mu$g is 0.140–0.145%.
[c]The average normal response for zearalane, 25$\mu$g is 0.100–0.110%.
[d]The average normal response for zearalanone, 12.54$\mu$g is 0.129%; and 25$\mu$g, 0.204%.

EXAMPLE 8

This example illustrates the anabolic activity of $O^4$-(2,3,4,6-tetra-O-acetyl-D-glucopyranosyl)-zearalenone when administered parenterally.

One dozen female Crossbred Kentucky lambs are used in the test. Six are used as the control and six are administered the test compound in the form of 12 mg. subcutaneous implants in their left ears. Each implant is cylindrical in shape, is 0.090 inch in diameter and 0.130 inch long, weighs 16 milligrams, and contains 4

BASAL RATION

| Finely ground corn cobs | 715 | lb. |
|---|---|---|
| Ground Corn | 330 | lb. |
| Alfalfa Meal | 300 | lb. |
| Dried Molasses, 85% | 120 | lb. |
| Soybean Meal, 44% | 300 | lb. |
| Dicalcium Phosphate | 14 | lb. |
| TM Salt | 10 | lb. |
| Premix* | 214 | lb. |
|  | 2003 | lb. |

| *Premix |  |  |
|---|---|---|
| Ground Corn | 202 | lb. |
| Limestone | 4 | lb. |

BASAL RATION-continued

| | | |
|---|---|---|
| Corn Oil | 2 | lb. |
| Vitamin E (20,000 IU/lb.) | 1 | lb. |
| Baciferm-40 | 1 | lb. |
| Vitamin A (30,000 IU/gm.) | 100 | gm. |
| Vitamin D₃ (200,000 IU/gm.) | 2 | gm. |
| BY-24 (Riboflavin) | 38 | gm. |
| Calcium Pantothenate | 22.2 | gm. |
| Niacin | 12.2 | gm. |
| Proferm (Vitamin B₁₂) | 188.8 | gm. |

EXAMPLE 9

This example illustrates the anabolic activity of $O^4$-(2,3,4,6-tetra-O-acetyl-D-glucopyranosyl)-zearalenone when administered orally.

Six female Crossbred Kentucky lambs are used in the test. Three are used as the control and three are administered the test compound in their feed at a concentration of 4.8 grams per ton of feed. Water and basal ration (the same as in Example 8) are provided ad libitum. Individual weights and feed conversions are obtained every two weeks. After 6 weeks, the test is completed and the data analyzed by appropriate statistical methods. The analysis shows a 20.1 percent greater weight gain response in those ewes which were fed the supplemental feed than in the control.

EXAMPLES 10 to 14

The procedure of Example 1 is essentially repeated except employing a Zearlin having the formula

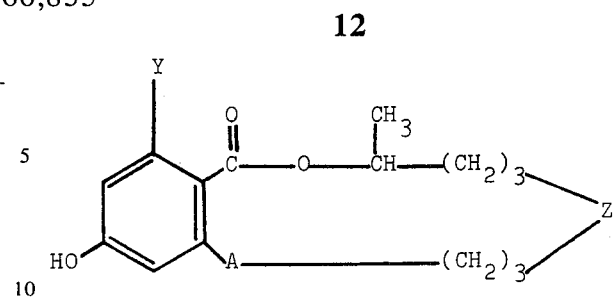

and a glycosyl bromide having the formula

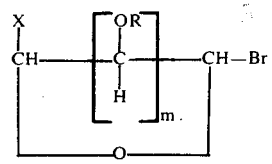

to provide a compound of the formula

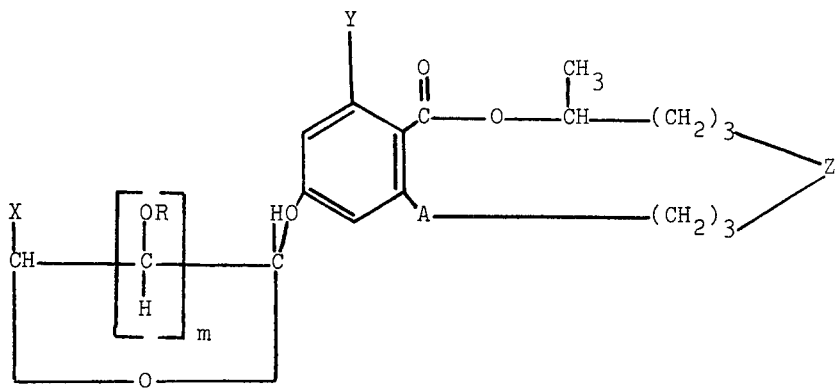

The values of R, X, Y, m, A and Z are provided in Table III. The product compounds of this example are administered orally to female cross-bred Kentucky lambs in accordance with the procedure of Example 9, to improve their growth rate.

TABLE III

| | Values for Starting Compound and Product | | | | | |
|---|---|---|---|---|---|---|
| | Y | X | R | m | A | Z |
| 10 | —OCH₃ | —CH₂OH | H | 3 | —CH₂—CH₂— | >CH₂ |
| 11 | —Obenzyl | —CH₂O—C(=O)CH₃ | —C(=O)—CH₃ | 3 | —CH₂—CH₂— | >CHOH |
| 12 | —OH | —CH₂OC₆H₅ | benzyl | 2 | —CH=CH— | >C=O |
| 13 | —OC(=O)C₂H₅ | —CH₂OC(=O)C₂H₅ | —C(=O)—C₂H₅ | 3 | —CH₂—CH₂— | >C=O |
| 14 | —OC₃H₅ | [OCH₃ / —C— / H] —CH₂OCH₃ | — CH₃ | 2 | —CH₂CH₂— | >CHOH |

EXAMPLE 15

The procedure of Example 5 is essentially repeated except employing zearalanone corresponding to the R conformer to provide O⁴-(2,3,4,6-tetra-O-acetyl-D-glucopyranosyl)-(R)-zearalanone. The product compound is administered orally to female Crossbred Kentucky lambs in accordance with the procedure of Example 9, to improve their growth rate.

EXAMPLE 16

The procedure of Example 1 is essentially repeated except employing cis-zearalanone to provide O⁴-(2,3,4,6-tetra-O-acetyl-D-glucopyranosyl)-cis-zearalanone. The product compound is administered orally to female Crossbred Kentucky lambs in accordance with the procedure of Example 9, to improve their growth rate.

Various modifications or equivalents will be apparent to one skilled in the art, and may be made in the present invention without departing from the spirit or scope thereof, and is, therefore, to be understood that these modifications or equivalents are within the scope of the present invention.

It is claimed:

1. A compound of the formula

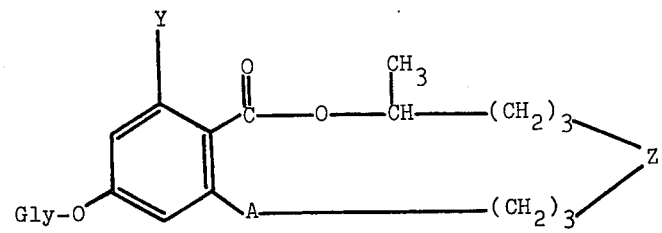

wherein —A— is either —$CH_2$—$CH_2$— or —CH=CH—; >Z is either >$CH_2$, >C=O or >CH—OH; Y is —H or —OR' wherein R' is hydrogen, lower alkyl, lower alkanoyl, or monocyclic aryl lower-alkyl of about 7 to 15 carbon atoms; and Gly is a glycosyl group having about 4 to 5 ring carbon atoms.

2. The compound of claim 1 wherein Gly has the formula

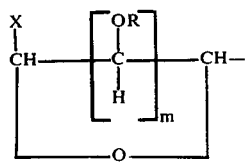

wherein X is —H or —(CHOR)$_n$CH$_2$OR, wherein $n$ is 0, 1 or 2; $m$ is 2 or 3; and R is selected from the group consisting of —H; NO$_2$; lower alkyl; lower alkanoyl; and monocyclic aryl lower-alkyl of about 7 to 15 carbon atoms.

3. The compound of claim 2 wherein Y is —OR', $n$ is 0, and $m$ is 3.

4. The compound of claim 3 wherein R is H or lower alkanoyl and R' is hydrogen.

5. The compound of claim 4 wherein R is lower alkanoyl.

6. The compound of claim 4 wherein R is

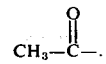

7. The compound of claim 5 wherein —Z— is >C=O and —A— is —CH=CH—.

8. The compound of claim 5 wherein —Z— is >C=O and —A— is —$CH_2$—$CH_2$—.

9. The compound of claim 5 wherein —Z— is >CH—OH and —A— is —$CH_2$—$CH_2$—.

10. The compound of claim 5 wherein —Z— is >$CH_2$ and —A— is —$CH_2$—$CH_2$—.

11. The compound of claim 4 wherein R is H.

12. The compound of claim 11 wherein —Z— is >C=O and —A— is —CH=CH—.

13. A compound of the formula

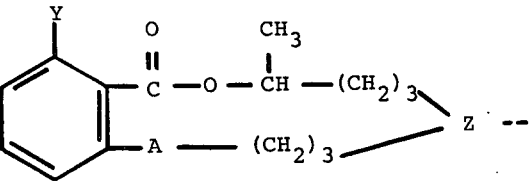

wherein —A— is either —$CH_2$—$CH_2$— or —CH=CH—; >Z is either >$CH_2$, >C=O, or >CH—OH; Y is —H or —OR' wherein R' is hydrogen, lower alkyl, lower alkanoyl, or monocyclic aryl lower-alkyl of about 7 to 15 carbon atoms; X is hydrogen or —(CHOR)$_n$CH$_2$OR, wherein $n$ is 0, 1 or 2 and R is hydrogen, lower alkyl, lower alkanoyl or monocyclic aryl lower-alkyl of about 7 to 15 carbon atoms.

14. The compound of claim 13 in which R is H or lower alkanoyl.

15. A compound of the formula

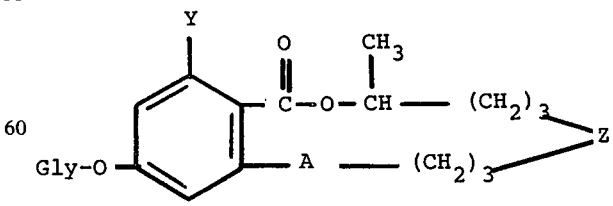

wherein —A— is either —$CH_2$—$CH_2$— or —CH=CH—; >Z is either >$CH_2$, >C=O or >CHOH; Y is —H or —OR' wherein R' is hydrogen, lower alkyl, lower alkanoyl, or monocyclic aryl lower-alkyl of about 7 to 15 carbon atoms; and Gly is 2, 3, 4, 6-tetra-0-acetyl-D-glucopyranosyl.

16. A compound of the formula
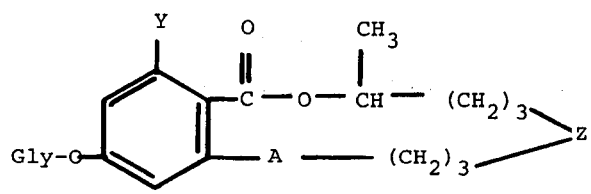
wherein —A— is either —CH$_2$—CH$_2$— or —CH=CH—; >Z is either >CH$_2$, >C=O or >CHOH; Y is —H or —OR' wherein R' is hydrogen, lower alkyl, lower alkanoyl, or monocyclic aryl lower-alkyl of about 7 to 15 carbon atoms; and Gly is glucopyranosyl.
* * * * *